United States Patent
Schirmer et al.

(10) Patent No.: US 7,186,565 B2
(45) Date of Patent: Mar. 6, 2007

(54) SAMPLING AND TOXICITY MONITORING DEVICE AND METHOD

(76) Inventors: Kristin Schirmer, Zum Kleingartenpark 33b, Leipzig (DE) 04318; Niels Bols, 156 Stonehaven Drive, Waterloo, Ontario (CA) N2L 6C5; Mario Schirmer, Zum Kleingartenpark 33b, Leipzig (DE) 04318

( * ) Notice: Subject to any disclaimer, the term of this patent is extended or adjusted under 35 U.S.C. 154(b) by 384 days.

(21) Appl. No.: 09/908,690

(22) Filed: Jul. 20, 2001

(65) Prior Publication Data

US 2003/0017614 A1    Jan. 23, 2003

(51) Int. Cl.
*C12Q 1/18* (2006.01)
*C12Q 1/20* (2006.01)

(52) U.S. Cl. ............... 436/178; 422/101; 422/102; 435/29; 435/32; 435/33

(58) Field of Classification Search ............... 436/178; 435/32–33, 4, 5, 8–30; 422/69, 86, 88, 101, 422/102
See application file for complete search history.

(56) References Cited

U.S. PATENT DOCUMENTS

| | | | | |
|---|---|---|---|---|
| 4,269,804 A | * | 5/1981 | Kring | 422/86 |
| 4,327,575 A | * | 5/1982 | Locker | 73/31.02 |
| 4,680,165 A | * | 7/1987 | Vo-Dinh | 422/88 |
| 4,790,857 A | * | 12/1988 | Miksch | 95/45 |
| 5,098,573 A | | 3/1992 | Huckins et al. | |
| 5,135,656 A | | 8/1992 | Means et al. | |
| 5,395,426 A | | 3/1995 | Huckins et al. | |
| 5,413,915 A | | 5/1995 | Case et al. | |
| 5,447,688 A | * | 9/1995 | Moore | 422/56 |
| 5,834,633 A | | 11/1998 | Davison | |
| 5,998,214 A | * | 12/1999 | Guirguis | 436/165 |
| 6,042,787 A | | 3/2000 | Pawliszyn | |
| 6,110,661 A | | 8/2000 | Lajoie et al. | |

FOREIGN PATENT DOCUMENTS

| | | |
|---|---|---|
| DE | 19726813 | 11/1998 |
| DE | 19830413 A1 | 9/1999 |
| EP | 0915329 | 5/1999 |
| GB | 2353860 | 3/2001 |
| WO | WO 9511989 | 5/1995 |
| WO | WO 98/33058 | 7/1998 |

OTHER PUBLICATIONS

SETAC 19th Annual Meeting: *The Natural Connection: Environmental Integrity and Human Health*. Abstract Book. Nov. 15-19, 1998. Charlotte, NC.

SETAC-Europe 9th Annual Meeting: *Quality of Life and Environmental in Cultured Landscapes*. Abstracts. May 25-29, 1999. Leipzig, Germany.

(Continued)

*Primary Examiner*—Jan M. Ludlow
(74) *Attorney, Agent, or Firm*—Bereskin & Parr

(57) ABSTRACT

A method and apparatus for testing an aqueous or gaseous environment for the presence of at least one chemical is provided in order to determine the toxicity of the chemical and optionally, the quantity and identity of the chemical.

36 Claims, 9 Drawing Sheets

Steps that may be used to initiate toxicity tests after sampling

Surface coated with chemical(s) that sorbed during sampling period

Add biological indicator, e.g. animal cells that adhere to the sampler surface

Individual chambers or series of chambers can be analyzed in multiwell plate formats, e.g. using fluorescent indicator dyes and multiwell plate readers

• Sampler chambers can be frozen and shipped prior to exposures

• Chemical(s) become bioavailable through processes such as desorption from the sampler surface by culture medium; solubilization through medium components, such as serum; phagocytosis

OTHER PUBLICATIONS

Arthur, C.L.; Pawliszyn, J: "Solid Phase Microextraction with Thermal Desorption Using Fused Silica Optical Fibers." *Anal. Chem*, 1990. 62. 2145-2148.

Baun, A; Jensen, S.D.; Bjerg, P.L.; Christensen, T.H.; Nyholm, N: "Toxicity of Organic Chemical Pollution in Groundwater Downgradient of a Landfill." *Environ. Sci. Technol*, 2000. 34, 1647-1652.

Bitton, G; Koopman, B: "Bacterial and Enzymatic Bioassays for Toxicity Testing in the Environment." *Reviews of Environmental Contamination and Toxicology*, 1992. 125, 1-22.

Bols, N.C; Schirmer, K; Joyce, E.M; Dixon, D.G; Greenberg, B.M; Whyte, J.J: "Ability of Polycyclic Aromatic Hydrocarbons to Induce 7-Ethoxyresorufin-o-deethylase Activity in a Trout Liver Cell Line." *Ecotoxicology and Environmental Safety*, 1999. 44, 118-128.

Bosveld, A.T.C; Kennedy, S.W; Seinen, W; Van Den Berg, M: "Ethoxyresorufin-o-deethylase (EROD) inducing potencies of planar chlorinated aromatic hydrocarbons in primary cultures of hepatocytes from different developmental stages of the chicken." *Arch Toxicol*, 1997. 71, 746-750.

Cronin, M.T.D; Schultz, T.W: "Validation of *Vibrio fisheriacute* toxicity data: mechanism of action-based QSARs for non-polar narcotics and polar narcotic phenols." *The Science of the Total Environment*, 1997. 204, 75-88.

Fairchild, J.F; Ruessler, D.S; Haverland, P.S; Carlson, A.R: "Comparative Sensitivity of *Selenastrum capricornutun* and *Lemna minor* to Sixteen Herbicides." *Arch. Environ.Contam.Toxicol*, 1997. 32, 353-357.

Grant, G.M; Shaffer, K.M; Kao, W.Y; Stenger, D.A; Pancrazio, J.J: "Investigation of *In vitro* toxicity of Jet Fuels JP-8 and Jet A." *Drug and Chem. Toxicol*, 2000. 23(1), 279-291.

Haubenstricker, M.E; Meier, P.G; Mancy, K.H; Brabec, M.J: "Rapid Toxicity Testing Based on Yeast Respiratory Activity." *Bull. Environ. Contam Toxicol*, 1990. 44, 669-674.

Hestermann, E.V; Stegeman, J,J; Hahn, M.E: "Serum Alters the Uptake and Relative Potencies of Halogenated Aromatic Hydrocarbons in Cell Culture Bioassays." *Toxicological Sciences*, 2000. 53, 316-325.

Huckins, J.N; Manuweera, G.K; Petty, J.D; Mackay, D; Lebo, J.A: "Lipid-Containing Semipermeable Membrane Devices for Monitoring Organic Contaminants in Water." *Environ. Sci. Technol*, 1993. 27, 2489-2496.

Longman, S.M; Buehring, G.C: "A Method for Measuring Steroid Adsorption to Tissue culture Plasticware." *Journal of Tissue Culture Methods*, 1986. 10(4), 253-255.

Martin, H; Piepenbank, M; Grathwohl, P: "Ceramic Dosimeters for Contaminant Monitoring." *University of Tubingen, Geological Institute, AppliedGeology Group, GERMANY*. 8 pages.

Sabaliunas, D; Ellington, J; Sabaliuniene, I: "Screening Bioavailable Hydrophobic Toxicants in Surface Waters with Semiprmeable Membrane Devices: Role of Inherent Oleic Acid in Toxicity Evaluations." *Ecotoxicology and Environmental Safety*, 1999. 44, 160-167.

Safe, S; Pihl, D: "Polychlorinated Biphenyls (PCBs), Dibenzo-p-Dioxins (PCDDs), Dibenzofurans (PCDFs), and Related Compounds: Environmental and Mechanistic Considerations Which Support the Development of Toxic Equivalency Factors (TEFs)." *Critical Reviews in Toxicology*, 1990. 21(1), 51-88.

Schirmer, K; Tom, D.J; Bols, N.C; Sherry, J.P: "Ability of Fractionated Petroleum Refinery Effluent to Elicit Cyto- and Photocytotoxic Responses and to Induce 7-Ethoxyresorufin-O-deethylase Activity in Fish Cell Lines." *The Science of the Total Envoronment*, 2001. 271, 61-78.

Schirmer, K; Chan, A.G. J; Bols, N.C: "Transitory Metabolic Disruption and Cytotoxicity Elicited by Benzo[a]pyrene in Two Cell Lines from Rainbow Trout Liver." *J. Biochem. MolecularToxicology*, 2000. 14(5) 262-276.

Schirmer, K; Herbrick, J-A.S; Greenberg, B.M; Dixon, D.G; Bols, N.C: "Use of Fish Gill Cells in Culture to Evaluate the Cytotoxicity of Photocytotoxicity of Intact and Photomodified Creosote." *Environmental Toxicology and Chemistry*, 1999. 18(6), 1277-1288.

Schirmer, K; Chan, A.G. J; Greenberg, B.M; Dixon, D.G; Bols, N.C: "Ability of 16 Priority PAHs to be Photocytotoxic to a Cell Line from the Rainbow Trout Gill." *Toxicology*, 1998. 127, 143-155.

Schirmer, K; Chan, A.G. J; Greenberg, B.M; Dixon, D.G; Bols, N.C: Methodology for Demonstrating and Measuring the Photoxicity of Fluoranthene to Fish Cells in Culture. *Toxicology in Vitro*, 1997. 11, 107-119.

Scroggins, ; Rodrigue, D. Tenth Symposium on Environmental Toxicology and Risk Assessment: Science, Policy, and Standardization—Implications for Environmental Decisions. Apr. 10-12, 2001. Toronto, Ont.

Wang, W.: "Literature Review on Duckweed Toxicity Testing." *Environmental Research*, 1990. 52, 7-22.

Whitlock, J.P. Jr: "Induction of Cytochrome P4501A1". *Annu.Rev. Pharmacol. Toxicol*, 1999. 39, 103-25.

PCT Search Report for PCT/CA02/01096 (Bols et al.) dated Jul. 4, 2003.

* cited by examiner

Figure 1.
Differences between time-integrated and snap-shot sampling

Time-integrated sampling

- Based on non-equilibrium partitioning
- Closed sampler design (membrane)
- Long exposure periods (days to months; accomplished through increased sorptive capacity)
- Represents concentration of substance(s) present during entire sampling period

Snap-shot sampling

- Based on equilibrium partitioning
- Open sampler design
- Short exposure periods (seconds to hours; time may be decreased through active stirring)
- Represents concentration of substance(s) present at sampling time

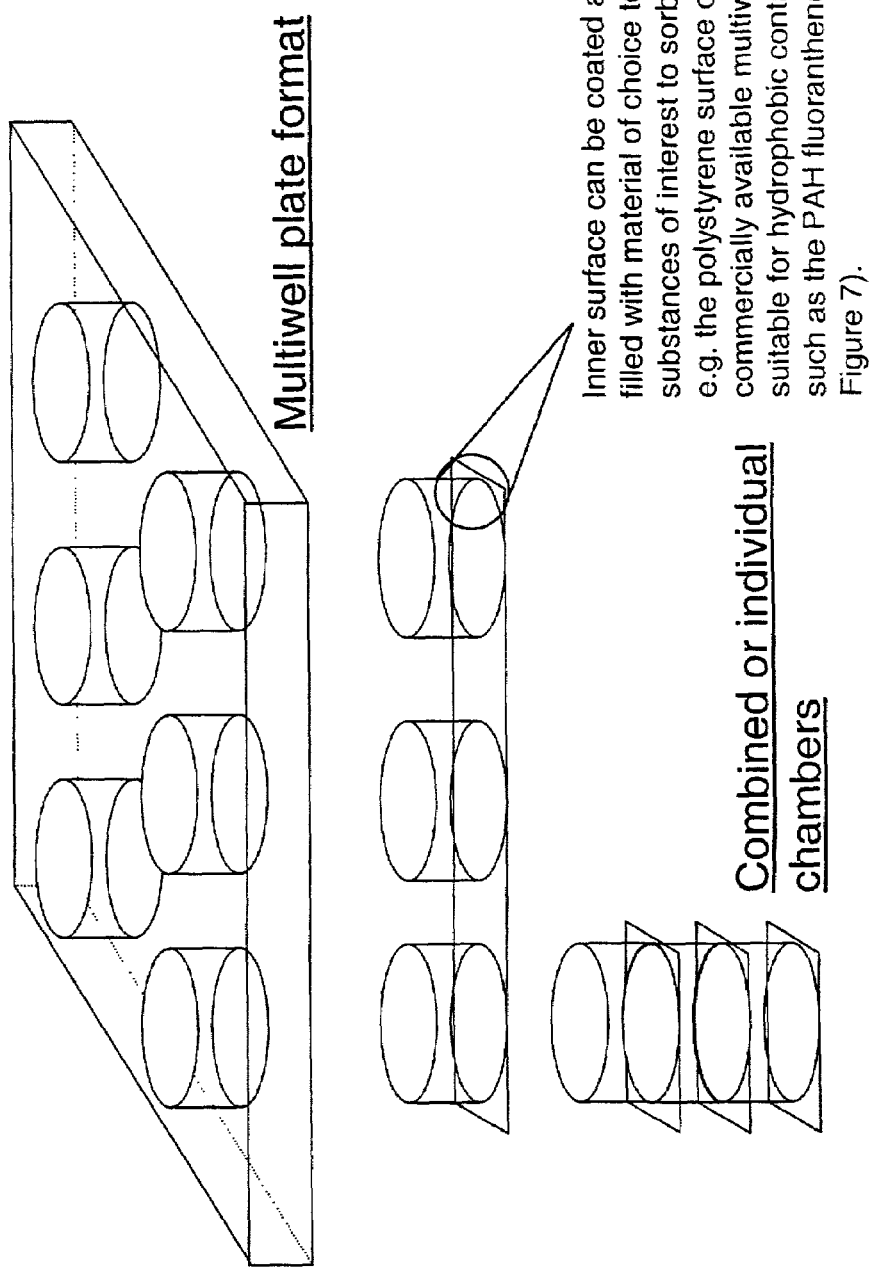
Figure 2. Possible arrangement of the chambers of the sampling device

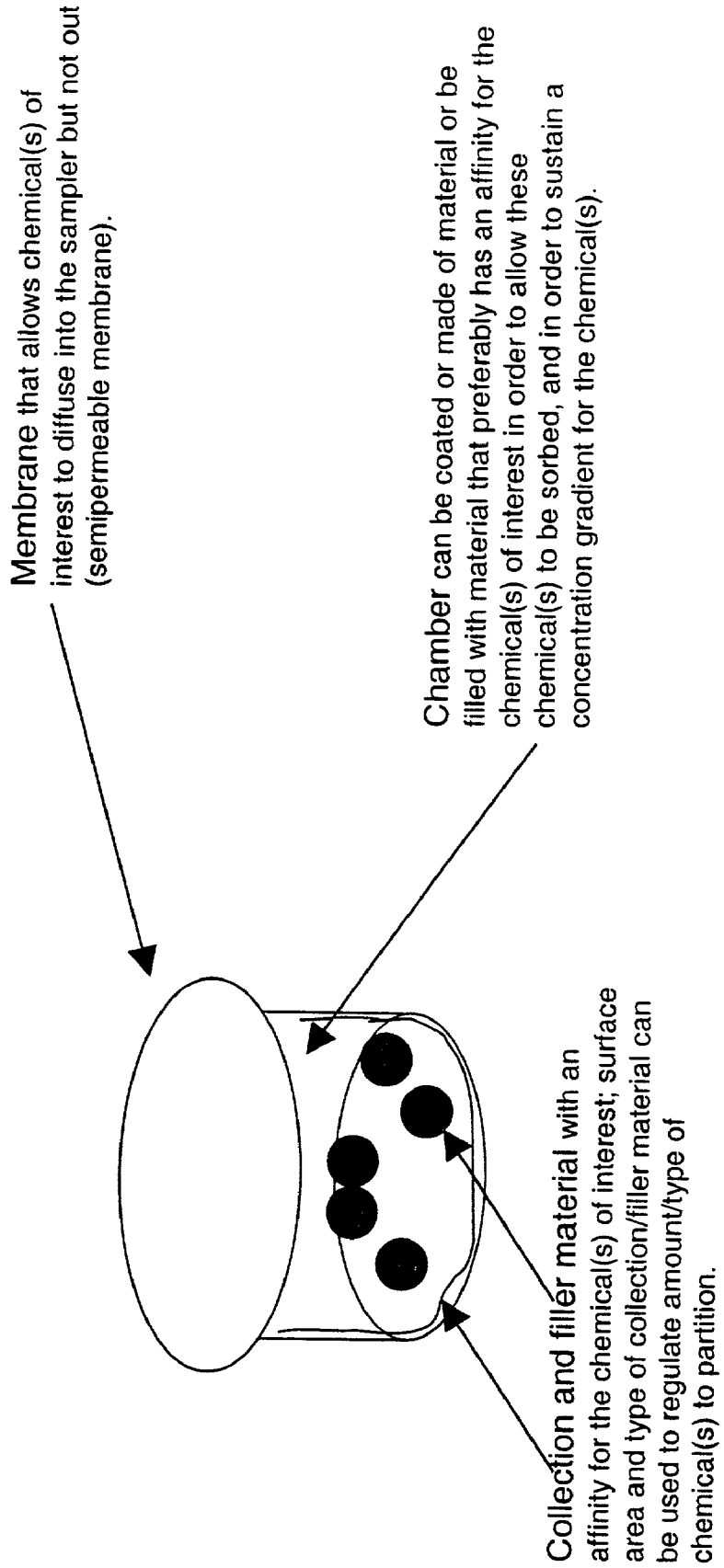
Figure 3. Sampling device for time-integrated sampling

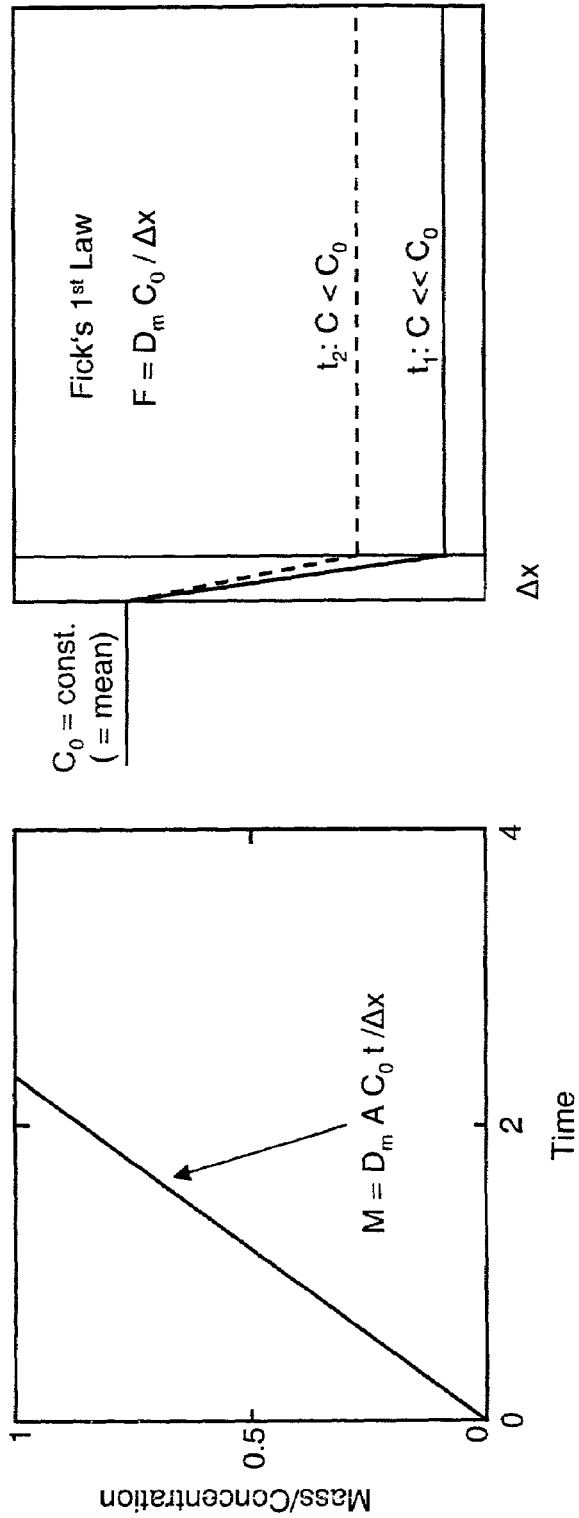

Figure 4.
Application of Fick's first law for time-integrated sampling

Diffusion across a membrane is approximated by Fick's first law where $M$, $D_m$, $A$, $C_0$, $t$, $\Delta x$, $F$, $C$ are the cumulative mass, the solute diffusion coefficient within the membrane, the cross sectional area of the membrane, the mean solute concentration outside the membrane, the sampling time, the thickness of the membrane, the mass flux through the membrane and the concentration inside the sampler. $D_m$, $A$, $t$, $\Delta x$, $F$, have to be determined for each sampler design. $M$ can be determined after sampling by means of chemical analysis. Given these parameters, $C_0$, the mean solute concentration outside the membrane, can be calculated.

Use of sorbent fillings to obtain dose-response relationships for time-integrated sampling Figure 6. Steps that may be used to initiate toxicity tests after sampling

Ability of adsorbed B[k]F to elicit EROD induction

Reduced matrix effects and ability of adsorbed oil refinery effluent to elicit EROD induction

US 7,186,565 B2

SAMPLING AND TOXICITY MONITORING DEVICE AND METHOD

FIELD OF INVENTION

This invention relates to the field of environmental sampling and, more particularly, monitoring industrial effluents and aquatic and gaseous environments, and methods and devices for conducting field testing.

BACKGROUND OF INVENTION

Aquatic environments are often contaminated by chemicals that are toxic. This has led to monitoring industrial effluents and aquatic environments with analytical chemistry methods and toxicity tests. However, for current monitoring programs, which are based on removing a certain volume of water at one-point-in-time (snap-shot sampling), several difficulties exist. Snap-shot sampling does not yield any information regarding the concentration of potentially harmful substances present in the period between samplings. As well, the complex matrix of many environmental samples can mask the effects of toxic substances (Baun et al., 2000) and/or make identifying the toxicant(s) impossible. Another difficulty lies in concentrating and extracting potentially harmful substances from large volumes of water in order to make them detectable through either chemical analysis or toxicity tests.

Three recent technological developments overcome some of the current monitoring problems. First, solid phase microextraction (SPME) technology allows for rapid and selective capture of chemicals onto fibers, which can subsequently be inserted into a chromatograph where sorbed chemicals are made available for chemical analysis through thermal desorption (Arthur and Pawliszyn, 1990, U.S. Pat. No. 6,042,787). Thus, SPME eliminates the need to take, transport and process water samples, and, at the same time, circumvents matrix problems for chemical analysis. However, although SPME permits the analysis of snap-shot samples it does not allow for time-integrated sampling.

A second technology that overcomes some of the problems of conventional monitoring procedures is a semipermeable membrane device (SPMD) (U.S. Pat. Nos. 5,098,573 and 5,395,426; see also Huckins et al., 1993). SPMDs are essentially plastic bags filled with fat (triolein) where the fat serves as a reservoir for hydrophobic contaminants to partition into. After being placed into aquatic environments of interest for a period of time (days to weeks), the SPMDs are removed and extracted to obtain the contaminants for chemical analysis and/or toxicity tests. Thus like SPME devices, SPMDs eliminate the sampling and processing of large volumes of water and circumvent matrix problems by selectively accumulating chemicals. An additional advantage of SPMDs is that they can be used to accumulate contaminants over time for extended periods such that average water concentrations for time intervals rather than time points can be determined. Distinct disadvantages of SPMDs are that they are expensive, extraction time- and solvent-consuming.

Finally, the third technological development that overcomes some of the current problems in environmental monitoring is the Dosimeter developed by Grathwohl and his group (German Patent application No. DE 198 30 413 A1; see also Martin et al., 1999). As with SPMDs, the Dosimeter functions by providing a large reservoir for chemicals of interest so that these chemicals can be accumulated over extended periods. For example, beads with high affinity for hydrophobic chemicals are placed into a ceramic tubing. Through the length of the tubing and the surface area of the beads, gradient-driven sorption is accomplished for weeks to months. Extraction of the Dosimeter is more straight forward than for the SPMD but is still required. As well, because of its design, the Dosimeter appears to be easier to modify in order to accommodate chemicals that are less likely to accumulate into fat.

SUMMARY OF THE INVENTION

The technological advances of the sampling and exposure device and methods of the present invention provide a competitive edge. By collecting, and concentrating the chemical(s) of interest, the device will reduce the expense of extracting large samples for toxicity testing and for chemical analysis. Accordingly, whether the device is used for obtaining snap-shot samples or for long-term, time-average samples, the device simplifies handling and analysis by concentrating the chemical(s) of interest at the time of collection. The device and methods of the invention eliminate the costly shipping of large samples, such as effluent water samples, from distant sources to the toxicity testing facilities because the devices would be relatively small and inexpensive to ship.

If the device is used for obtaining long term, time average samples, then, through time-integrated sampling, the number of tests will be reduced and information will be available on the presence and/or concentration of the substance(s) of interest in the period between samplings.

Since the device and methods may utilize small volumes, toxicity assays may be done with small biological indicators, such as animal cells or invertebrates, which satisfies a societal desire to reduce the use of whole animals in toxicity testing. As well, biological molecules, such as receptors or nucleic acids, may be used to detect chemicals of a certain structure or effect. Through the use of the biological reporters, toxicity information may be obtained rapidly and the range of toxicity endpoints expanded as required. The advantages of in vitro test systems are also increasingly recognized by governmental agencies and regulators. For example in Canada, a test that shall use in vitro cell cultures of rainbow trout is being considered as part of a governmental regulation for effluent testing by the year 2002 (Scroggins and Rodrigue, 2000).

The present invention, which overcomes the deficiencies of the prior art sampling devices and methods, provides a device and method which allow for time-integrated sampling and/or snap-shot sampling where there is no requirement for extraction (although extraction may be performed if desired) of accumulated chemicals, and as such is directly compatible with toxicity tests. The inventors have determined that it is possible to collect freely dissolved substances from aquatic or gaseous environments in a format that allows the chemicals to be immediately screened for their toxic potential.

In its broad aspect, the present invention provides a sampling and toxicity monitoring device.

According to one embodiment of the invention there is provided a sampling and toxicity monitoring device comprising;

(a) at least one chamber having a collection material for sorbing at least one chemical, wherein the chamber is able to support at least one reporter for subsequent toxicological analysis;

(b) at least one entry port to the chamber and (c) a semipermiable barrier covering said entry port for essentially unidirectional travel of the chemical into the chamber, wherein a concentration gradient exists across the barrier for the at least one chemical.

In one embodiment, the sorbent collection material is one or more of polystyrene, polydimethylsiloxane, glass, polyacrylate, XAD resins, polyurethane foam, and Amberlite In another embodiment, the device further comprises a filler material, the filler material is one or more of polystyrene, polydimethylsiloxane, glass, polyacrylate, XAD resins, polyurethane foam, and Amberlite.

In another embodiment, the chamber and the barrier define an enclosed space and the collection material is fixed to a surface of the chamber.

In another embodiment, the chamber and the barrier define an enclosed space and the collection material is removably received in the enclosed space as a unit.

In another embodiment, there is more than one chamber.

In another embodiment, the device further comprises a filler sorbent which is provided in at least one of the chambers.

In another embodiment, the device further comprises a filler sorbent which is provided in at least some of the chambers and a different amount of filler sorbent is present in at least some of the chambers.

In another embodiment, at least some of the chambers have at least one of a different filler sorbent and a different collection sorbent material.

In another embodiment, the chambers are provided in groups, each groups comprises a plurality of chambers and the amount of filler material is essentially the same in the chambers of each group and differs between the groups.

In another embodiment, the entry port of the at least one chamber is open when the device is in use to collect samples.

In accordance with another embodiment of this invention, there is provided a method for sampling and monitoring toxicity in an environment comprising the steps of:

(a) providing a device comprising a chamber with an entry port covered by a membrane and defining a space, the device having a collection material for adsorbing at least one chemical, and placing said device in an environment for a measured period of time;

(b) removing the device from the environment at the end of the measured period of time and adding a measured amount of a reporter to the space;

(c) incubating the reporter for a predetermined period of time;

(d) assaying the reporter for vitality or functionality to determine whether a chemical was sorbed in the chamber and caused a toxicological response.

In one embodiment, a further step of extracting the chemical from the sorbent and performing a chemical analysis of the substance to provide its concentration and identity is carried out.

In another embodiment, the method further comprises providing a filler sorbent to increase the sorptive capacity of the chamber.

In another embodiment, the device comprises a plurality of chambers and at least some of the chambers contain varying amounts of a filler sorbent and the chambers having the filler sorbent are treated to obtain a dose-response profile.

In another embodiment, the device comprises a plurality of chambers and only some of the chambers have a reporter provided therein wherein the method further comprises utilizing the chambers having the reporter to conduct toxicity testing and utilizing the chambers without the reporter to conduct chemical testing.

In another embodiment, the method further comprises providing a filler sorbent in at least some of the chambers.

In another embodiment, the method further comprises providing varying amounts of the filler sorbent in different chambers.

In another embodiment, the device comprises a plurality of chambers and the method further comprises providing a filler sorbent in some of the chambers.

In another embodiment, the method further comprises providing varying amounts of the filler sorbent in different chambers In another embodiment, the method further comprises providing a filler sorbent in at least some of the chambers.

In accordance with another embodiment of this invention, there is provided a method of determining the concentration of a substance in an environment comprising the steps of:

(a) placing a device comprising a chamber with an entry port covered by a membrane and defining a space, the device having a collection material for sorbing at least one chemical in the environment for a measured period of time;

(b) removing the device from the environment at the end of the measured period of time and adding a measured number of a reporter to a chamber of the device;

(c) incubating the reporter for a predetermined period of time;

(d) assaying the reporter for vitality or functionality to determine a quantity of a chemical adsorbed in the chamber; and, (e) calculating the concentration of the chemical in the environment based on the determination.

In one embodiment, the method further comprises extracting the chemical from the sorbent and performing a chemical analysis of the chemical to provide its concentration and identity.

In another embodiment, the method further comprises providing a filler sorbent to increase the sorptive capacity of the chamber.

In another embodiment, the device comprises a plurality of chambers and at least some of the chambers contain varying amounts of a filler sorbent and at some of the chambers having the filler sorbent are treated to obtain a dose-response profile.

In accordance with another embodiment of this invention, there is provided a method of determining the concentration of a substance in an environment comprising the steps of:

(a) placing a device having a collection material for sorbing at least one chemical in the environment for a measured period of time;

(b) removing the device from the environment at the end of the measured period of time;

(c) conducting a chemical analysis on the collection material itself.

In one embodiment, the chemical analysis of the collection material is conducted using a fluorescent plate reader.

In another embodiment, the collection material is provided in a chamber and the method further comprises providing a filler sorbent to increase the sorptive capacity of the chamber.

In another embodiment, the method further comprises providing at least some of the chambers contain varying amounts of the filler sorbent.

In another embodiment, the method further comprises providing different filler sorbents to different chambers.

In another embodiment, the collection material is provided in at least one chamber and the chamber comprises a measured number of a reporter and the method further comprises assaying the reporter for vitality or functionality to determine whether a chemical was sorbed in the chamber and caused a toxicological response.

In another embodiment, the collection material is provided in at least one chamber and the chamber comprises a measured number of a reporter and the method further comprises assaying the reporter for vitality or functionality to determine a quantity of a chemical sorbed in the chamber.

In another embodiment, the method further comprises calculating the concentration of the chemical in the environment based on the determination.

Other features and advantages of the present invention will become apparent from the following detailed description of the preferred embodiments of the invention. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which:

Table 1 compares snap-shot versus time-integrated sampling;

FIG. 1 illustrates the basic differences between time-integrated and snap-shot sampling;

FIG. 2 illustrates possible arrangements of the chambers that form the core of the sampling device;

FIG. 3 illustrates the sampling device for time-integrated sampling;

FIG. 4 illustrates the application of Fick's first law for time-integrated sampling;

DETAILED DESCRIPTION OF THE INVENTION

Figure 5:
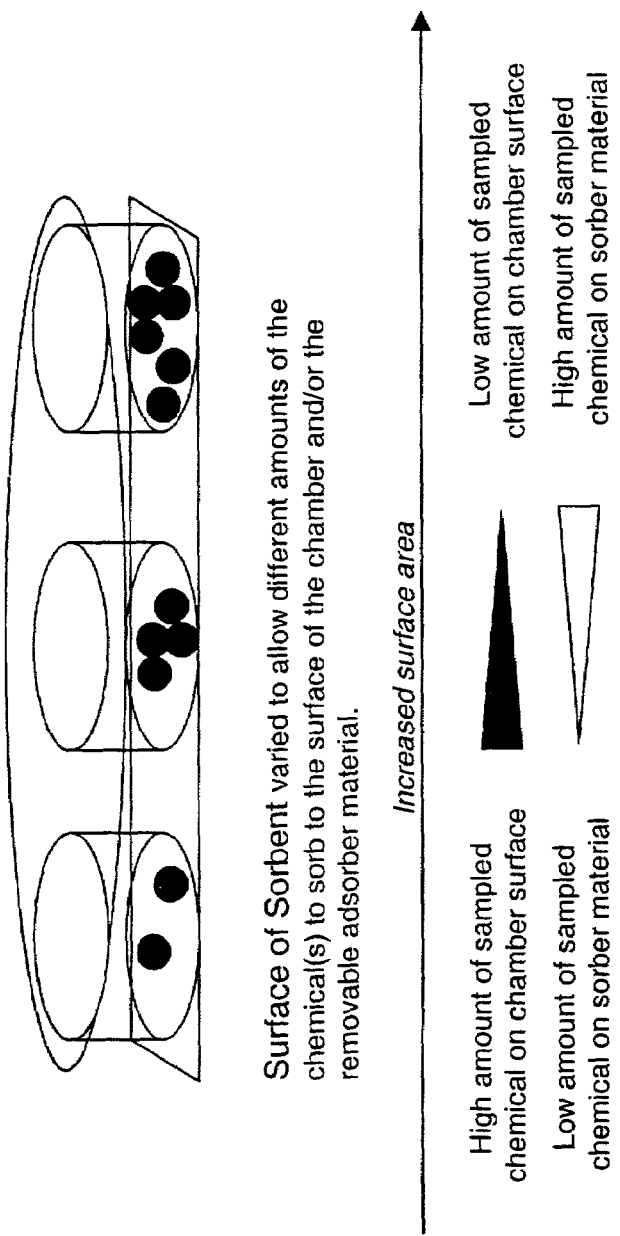
FIG. 5 illustrates how filling materials can be used to obtain dose-response relationships in subsequent toxicological tests.

As discussed above, the present inventors have developed a device and method to allow for either time-integrated or snap-shot sampling of chemicals in an aqueous or gaseous environment where there is no requirement for extraction of accumulated chemicals prior to toxicity tests. As such, the sampling device and method of the invention are directly compatible with toxicity tests.

In accordance with one aspect of the instant invention, the chemical(s) are collected in situ on a collection material so as to allow the direct testing of the collection material without extracting the chemicals from the collection material or without concentrating the sample. It will be appreciated that these additional steps may be applied to the samples obtained by using the device as described herein. In accordance with this-aspect, the collection may be conducted for snap-shot or time-integrated testing.

In accordance with another aspect of the instant invention, testing may be conducted in situ to determine whether a biological indicator is detrimentally affected by one or more chemicals being collected.

As used herein, the terms "chemical" or "chemicals" are the substances in the aqueous or gaseous environment which are being tested.

As used herein the term "chamber" means any space or container having a surface with or being built of a collection material. The collection material has an affinity to sorb one or more chemicals of interest. The collection material (sorbent) may be the material of the chamber itself. Alternatively, the collection material may be fixed to the surface of the chamber or space (such as by physical or chemical means) or it may be a separate component that is removable received in the chamber. For example, the sorbent may be a single mass of material which is removable from the container as a unit. In any case, the collection material presents at least one face where the sorbent is accessible by the gas or liquid which is to be sampled.

As used herein the term "filler material" means any material that has an affinity to sorb one or more chemicals of interest and that may be a separate component which is removable received in the chamber. For example, the filler material may be a plurality of discrete members (e.g. beads or the like) which are loosely placed in the chamber. The filler material may be the same as the collection material. The filler material is optionally provided to permit testing to obtain a dose response profile.

As used herein the term "array" means any pattern of chambers which facilitates tabulation of different conditions for collection of materials, such as, for example, different concentrations of sorbents or different types of sorbents or different types of reporters of toxicity.

As used herein, the term "fixed" means any method of maintaining an interaction between at least two substances, including the chemical substance which is being sorbed and the sorbent material, where the interaction includes chemical fixing by, for example, non-covalent forces such as hydrophilic, vanderwaals, hydrogen bond, hydrophobic, and/or electrostatic interaction.

As used herein, the term "snap-shot sampling" refers to a short-term accumulation (seconds to hours) of chemicals such that the chemicals are at equilibrium between the sampler surface(s) and the sampling environment. This is achieved by exposing the sampling device directly to the chemicals within the sampling environment (open sampler design, see FIG. 1, Table 1).

As used herein, the term "time-integrated sampling" refers to a long-term accumulation (days to months) of chemicals such that the chemicals never are at equilibrium with the sampler surface(s). This is achieved by providing a large sorptive capacity of the sampler and by exposing the sampling device indirectly, that is through a membrane, to the chemicals of the sampling environment (referred to herein as a "closed sampler design", see FIG. 1, Table 1).

As used herein "animal" means all members of the animal kingdom.

As used herein "plant" means all members of the plant world.

As used herein "biomolecule" means any biologically derived molecule or structure that specifically binds to certain chemicals or chemical classes.

As used herein "support" means the ability to hold vital cells either in suspension or by adherence.

As used herein the term "substance" includes the group of substances known as a chemical or chemicals.

The device of the invention is a sampling and exposure device for assessing responses in biological assays upon time-integrated sampling and/or snap-shot sampling. The device can be designed as one chamber or as a series of chambers, or an array of chambers such as would be present on tissue culture plates (FIG. 2). If a plurality of chambers are used, then the chambers may be an integral part of the structure of a sampling tray, such as is the case for a tissue culture. If the device is constructed for snap-shot sampling, then each "chamber" may be a flat surface. Alternately, the collection material may be provided in a three dimensional chamber. If the device is constructed for time-integrated sampling, then each chamber defines a space which is adapted to be enclosed so as to produce non-equilibrium conditions. The word "chamber" is used since in such cases, the chamber surrounds a substantial portion of a volume which may be subsequently closed off by a suitable closure membrane (e.g. it may be three dimensional). However, depending on the shape of the closure membrane (e.g. pyramidal) the chamber may be a flat sheet to which a three dimensional closure is attached. Further, individual chambers may be collected into a structure which provides any desirable array.

In accordance with one aspect of the instant invention, regardless of the number of chambers or the structure of the chambers, the chambers may be the collection material itself. The collection material is any material that may be directly tested for the presence of sorbed chemicals such as by fluorescent plate reader with scanning excitation and emission capability or by spectrophotometry. Such collection materials include plastics (e.g. polystyrene, polyacrylate), polydimethylsiloxane or glass. Alternately, the chambers may be constructed of non-sorbent materials such as aluminium, stainless steel or Teflon™ and be coated with the collection material, such as polydimethylsiloxane or polyacrylate or the chambers are at least partially filled with the collection material (e.g. polystyrene). In any case, the collection material is the material which is itself directly tested to determine the presence of toxic chemical(s) in the fluid being tested. Preferably, the collection material is an adsorbent.

Alternatively for time-integrated sampling, the chambers may contain any sorbent material known in the sampling art, such as XAD resins, Amberlite, PUF (polyurethane foam), plastics or glass (FIGS. 1 & 3). These fillings have several uses. First, they can be used specifically to vary the sorptive capacity, which preferably is great enough to prevent the formation of an equilibrium between the sampling environment and the interior of the chambers over the entire sampling period during time-integrated sampling (FIGS. 1 & 3). Further, they may be tested to determine the presence of toxic chemical(s) in the fluid. These filler sorbents can be tested either in the standard way known in the art (e.g extraction followed by known test procedures) or in the novel way as described for the collection material.

Thus two separate tests may be conducted at the same time. Further, differing amounts of the filler sorbent may be provided in different chambers of the same array. Thus the accumulation of chemical(s) in the fluid in each chamber may be varied. This is useful for obtaining dose-response relationships in subsequent toxicity tests.

A membrane is fitted onto the sampling chambers for time-integrated sampling (FIG. 3) and may have three functions. Firstly, the membrane will restrict the movement of chemicals into the chambers to diffusion. Based on diffusion, and given a sorptive capacity great enough to prevent the formation of an equilibrium between the sampling environment and the interior of the chambers over the entire sampling period, Fick's first law applies, that is chemicals sorb to the sorbent material and/or the sampler surface linearly with time (FIG. 4). In order to favour the essentially unidirectional movement of chemicals into a chamber, the membrane is, preferably, semipermeable.

If the chamber also contains a filler sorbent material, then another function of the membrane may be to hold the sorbent filling materials in a chamber, which, in addition to increasing the sorptive capacity of the chambers, can be used to establish different levels of sorbed chemicals on the fillings and/or the chamber surfaces over the exposure period (FIG. 5). Different levels of sorbed chemicals over an exposure period can be used to obtain dose-response relationships in subsequent toxicity tests.

Yet another function of the membrane may also be to protect the interior of a chamber from microbial growth or other means of contamination. Examples of membrane materials which may be used include ceramic membranes, such as a $MgAl_2O_4$ membrane, for sampling aqueous environments and gas permeable foils, such as bioFOLIE (Unisyn), for sampling gaseous environments. Any such membrane known in the art may be utilized.

If the device is used to obtain dose response relationships, then any animal, plant, algae, fungal, protozoan or bacterial cell or other vital cells or small organisms capable of living in/on the device can be a potential reporter of biological response and may be provided in one or more chambers. For example, cell cultures from mammals (Grant et al., 2000), birds (Bosveld et al., 1997) or fish (Schirmer et al., 2000a/b) may be used as reporters. As well, whole organisms may be used as reporters. Examples of these include duckweed (Wang, 1990), *selenastrum* (Fairchild et al. 1997), *Saccharomyces cerevisiae* (Haubenstricker et al., 1990), ,*Tetrahymena* (Lynn and Gilron, 1992), *daphnia* (Fairchild et al., 1997), and *Vibrio fisheri* (Cronin and Schultz, 1997). Alternatively, biomolecules (such as receptors) can be used as a reporter to recognize potentially harmful chemicals in a sample.

Figure 6:
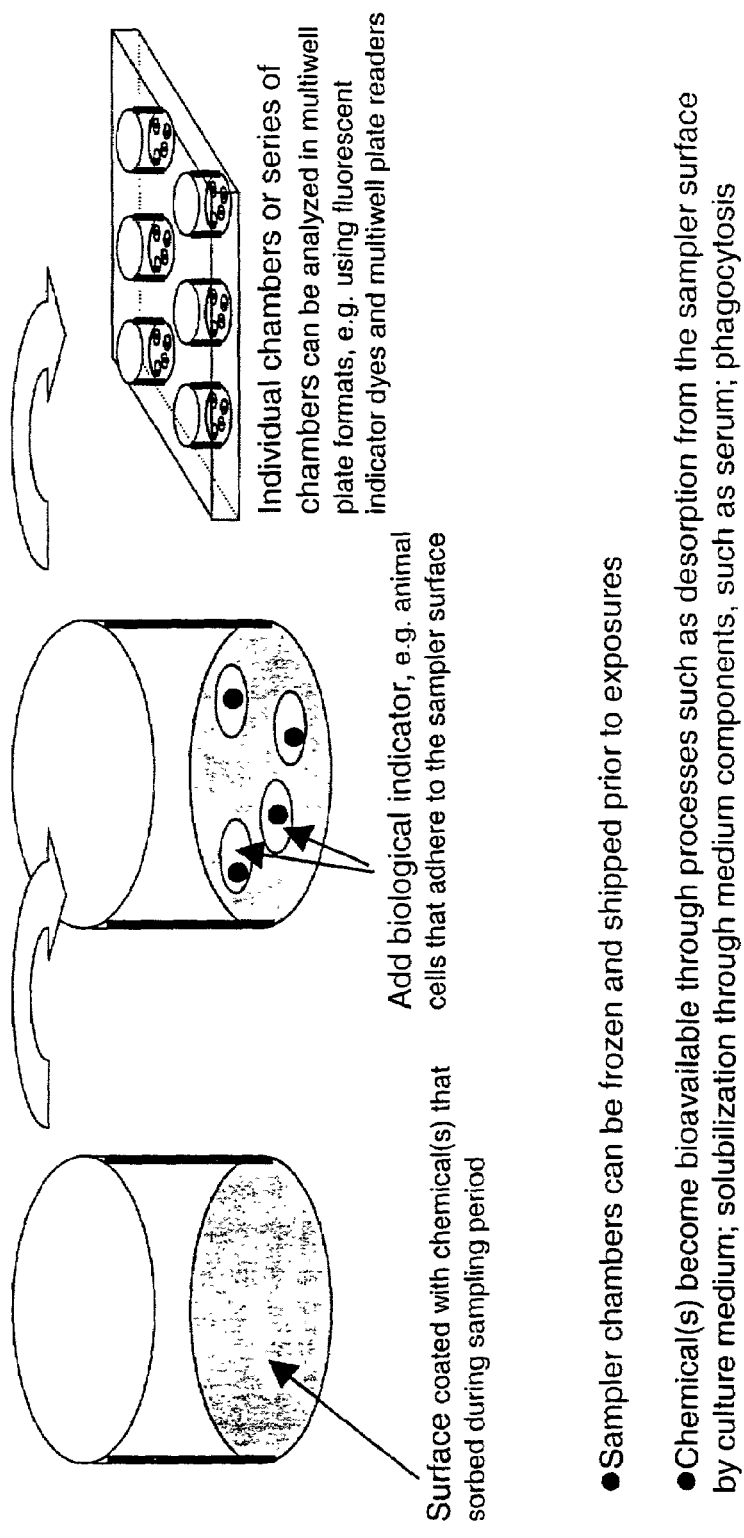
FIG. 6 illustrates the steps which may be used to initiate toxicity tests after sampling.

One distinct advantage of one aspect of the apparatus according to the present invention is that sorbed chemicals are made bioavailable to reporter cells or molecules. While not wishing to be bound by any one theory, the mechanism for bioavailability is believed to be by gradient-driven desorption or, possibly, by active uptake by the reporters. In any event, the presence of the reporter cells or molecules directly in or on the sampling device eliminates the need for solvent-extraction prior to biological analysis. The desorption step is initiated by adding the reporter cells or molecules in an appropriate liquid culture medium or buffer directly onto the surface or in suspension in each chamber of the sampling device, onto which chemicals will have sorbed during sampling (FIG. 6) (either snap-short or time-integrated sampling). An appropriate liquid culture medium is one that will maintain reporter cell vitality or reporter molecule integrity. For example, Minimal Essential Medium (MEM), Dulbecco's Minimal Essential Medium (DMEM) or Leibovitz' L-15 medium are typical media used for culturing animal cells (Catalogue of the American Type Culture Collection, 2000).

Figure 7:
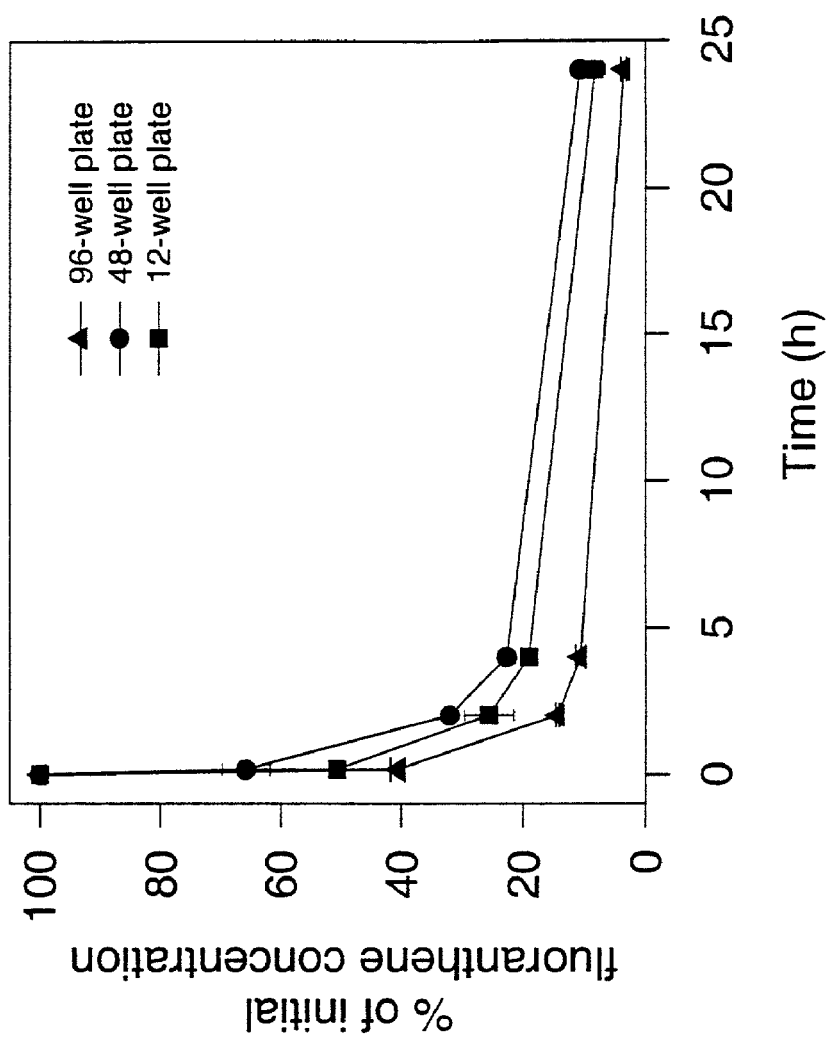
FIG. 7 shows the kinetic of sorption to the polystyrene of tissue culture plates of a model chemical, fluoranthene.

The type of chemicals sorbed will depend on the sampling environment and can be directed by means of different chamber materials, coatings or fillings. For example, polystyrene can be used to collect non-polar substances such as polycyclic aromatic hydrocarbons (FIG. 7). It will be readily appreciated by those skilled in the art that other materials may be selected depending on the chemical.

The type of biological indicator will depend on the outcome measures chosen, which can range from sublethal to lethal damage and from more integrated responses, like growth, to more specific responses, like enzyme induction or receptor binding. For example, the loss of motility of daphnids placed into a chamber onto which chemicals will have adsorbed would be a measure of lethality, whereas modulation of growth due to adsorbed chemicals of the algae Selenastrum would be an integrated sublethal response. While more integrated responses, like loss of motility and modulation of growth, generally do not reveal the mechanisms underlying toxicity, more specific but less integrated measures can give insight into toxic mechanisms and thus yield information regarding the chemical class of adsorbed substances. An example of this would be the ability of adsorbed chemicals to induce 7-ethoxyresorufin-O-deethylase (EROD) activity (FIG. 8), which is mediated by the aryl-hydrocarbon receptor and thus is dioxin- or dioxin-like compound-dependent (Whitlock, 1999).

In addition to direct biological analysis, chemical analysis can be carried out on the sampling and exposure chambers and actual chemical concentrations be calculated. One way of doing this is by conventional analytical methods. For both time-integrated as well as snap-shot sampling, sorbed chemicals may be desorbed by the addition of one or more known solvents, such as methanol, and concentrations of the chemicals determined by conventional analytical methods, such as high performance liquid chromatography. Alternatively, chemical analysis can be carried out directly on the collection material with a fluorescent plate reader with scanning excitation and emission capability or other direct analysis techniques. For snap-shot sampling, the concentrations determined, i.e. calculated based on the sorption isotherm, are the concentrations present at the time of sampling and should be the same as those determined by conventional water sampling and chemical analysis. For time-integrated sampling, the concentrations determined reflect the amount of chemicals adsorbed during the entire sampling period. Applying Fick's first law, these concentrations can be used to calculate the average concentrations of the substances during the entire sampling period (FIG. 4).

Figure 9:
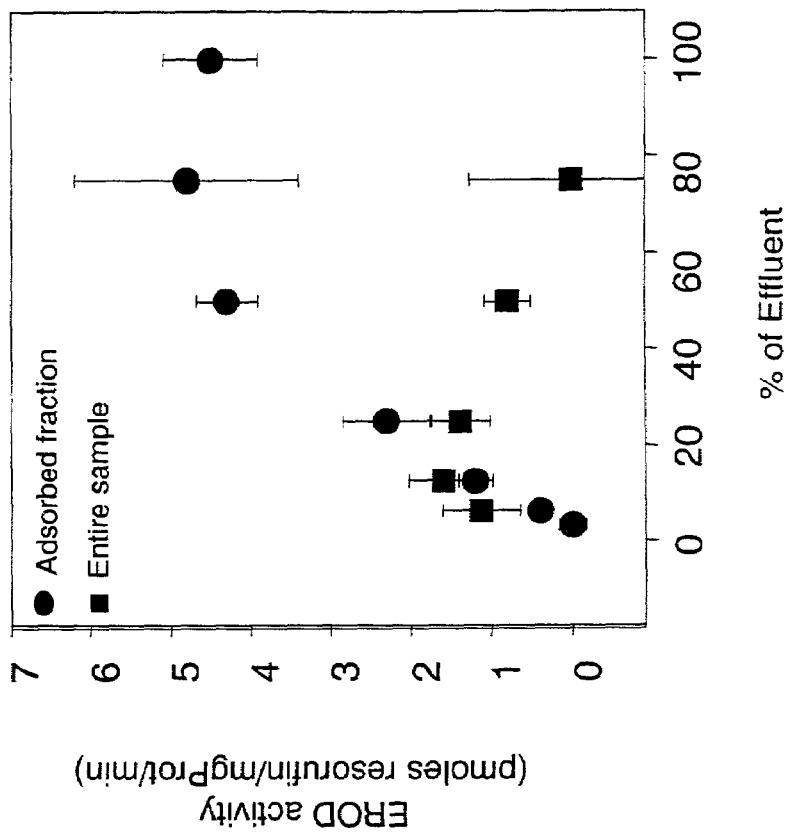

Snap-Shot Sampling:

Snap-shot sampling may be carried out as follows:

I. Small volumes of environmental samples are added directly to a sampler (a "chamber") according to the invention, the samples having been brought from the sample site to another location. The sampler is then exposed to the original, undiluted samples or to samples that have been diluted with water in order to obtain a concentration gradient (FIG. 9).

II. A second approach is that a sampler may be brought to the field and be exposed directly to the environment to be sampled. In this embodiment which may be referred to as an open sampler design, an equilibrium between the sampler surface and the environment to be sampled is reached quickly (FIG. 7). Upon sampling, the sampler surface is dried. Where only toxicity tests are carried out, all chambers of the sampling device can be used for these tests. Where chemical analysis is carried out in addition to toxicity tests, a number of chambers can be reserved, for example, with one half for toxicity tests and the other half for chemical analysis.

For toxicity tests, reporter cells or molecules are preferably added to chambers in an appropriate culture medium. An appropriate liquid culture medium is one that will maintain reporter cell vitality (or reporter molecule integrity) and support expression of a chosen endpoint in the toxicological test. For example for the experiment depicted in FIG. 8, liver cells from rainbow trout (RTL-W1 cells) were added in Leibovitz' L-15 medium that contained 5% fetal bovine serum as a supplement (Bols et al., 1999). The reporters are left to desorb or interact with the chemicals at the sampler surface for a predetermined time. In the example shown in FIG. 8, exposure time was 24 h which was sufficient for RTL-W1 cells to adhere to the surface and to respond to an exposure to dioxin or dioxin-like compounds with the induction of EROD activity (Bols et al., 1999). After a predetermined exposure time, the reporter cells are evaluated for the expression of toxicity. In the example shown in FIG. 8, cells were assayed for EROD activity (Bols et al., 1999). Other examples of toxicological endpoints would be the disruption of metabolic activity or the loss of cell membrane integrity in cultured cells, which can be measured using the fluorescent indicator dyes alamar Blue and CFDA-AM (Schirmer et al., 2000a/b), or the modulation of light emission in luminescent bacteria (Bitton and Koopman, 1992). Although not essential to the method, the arrangement of chambers in a multiwell plate format and the use of fluorescent indicator dyes or light emission is advantageous because of recent developments in automated fluorescence/luminescence multiwell plate readers. Plates with 6 to 386 wells can be analyzed in seconds. As well, the number of available fluorescent indicator dyes with different cellular targets is increasing rapidly, particularly with the aim of replacing radioactive markers. All such adaptations to sampling methods and counting may be used in the context of the present invention.

Toxicity tests indicate whether potentially harmful chemicals were accumulated by the sampling device during exposure to the sample or sampling environment. This information would be analogous to the results, for example, of the rainbow trout lethality test or the Daphnia magna motility test being conducted upon exposure to a snap-shot probe of industrial effluent. A distinct advantage is that, due to selective sorption by the sampling device, the probe is purposely fractionated prior to the toxicity test, which, among other advantages, diminishes matrix problems and guides the toxicity tests toward a particular class of chemical contaminants. For example, if EROD induction is chosen as an endpoint, the reference chemical for the EROD induction pathway, TCDD, can be run in parallel to the environmental sample and EC50 values for both dose-response curves (environmental sample and TCDD) be obtained. The EC50 values can then be used to calculate the bioassay-derived toxicity equivalent-, or TCDD-equivalent-, factor (TEF) of the environmental sample. This is done by dividing the EC50 for TCDD by the EC50 obtained under the same assay conditions for the sample, and is a measure of the potency of the sample to act through the aryl hydrocarbon receptor pathway in the same manner as TCDD. If, in addition to the toxicological and indirect chemical analysis, direct chemical information for individual chemicals is required, the sampling chamber(s) reserved for chemical analysis can be used.

Chemical analysis can be carried out on the sampling and exposure chambers and actual chemical concentrations may be calculated. One way of doing this is by conventional analytical methods. Sorbed chemicals are desorbed by the addition of a solvent, such as methanol, and concentrations of the chemicals determined by conventional analytical methods, such as high performance liquid chromatography. Alternatively, chemical analysis can be carried out with a fluorescent plate reader with scanning excitation and emission capability, or with a spectrophotometer. The concentrations determined, i.e., calculated based on the sorption isotherm, correspond to the concentrations present at the time of (snap-shot-) sampling.

In addition to knowledge of the concentrations of compounds for which the analysis is conducted, the combination of toxicological testing with chemical analysis can indicate the presence of toxic chemicals not yet analysed for and thus guide further testing and identification. One way of pursuing this is through the use of the toxic equivalency approach. Central to this approach is the derivation of toxic equivalency factors (TEFs) of individual chemicals relative to a standard compound, such as TCDD (Safe, 1990) or fluoranthene (Schirmer et al., 1999, 1998a). Using the TEF, the concentration of a chemical, determined through chemical analysis, can be converted into the concentration of the standard chemical that would produce the same response. In this way, the concentrations of individual chemicals known to be present on the sampling device can be expressed as toxic equivalent concentrations of the standard chemical and added together to give a single toxic equivalent concentration (TEC). If this chemistry-derived TEC explains only part of the toxicity observed on the sampling device, i.e., is smaller than the bioassay-derived TEC obtained on the sampling device (see above), chemicals that have not yet been analysed for chemically must be present. These can be identified by a more detailed chemical analysis and by testing identified chemicals upon sorption to the sampling device for their contribution in subsequent toxicological tests.

Time-Integrated Sampling:

According to this embodiment of the invention, a sampler according to the present invention is placed into the sampling environment and left for a period of time (e.g days or months) to accumulate chemicals. By virtue of the closed sampler design, chemical uptake will be restricted to diffusion and a large concentration gradient can be maintained through the use of the optional sorbent fillings (FIG. 3) so that chemicals adsorb to the sampler interior according to Fick's first law (FIG. 4). In order to obtain a concentration gradient for subsequent toxicological tests, various amounts of sorbent material can be used to fill the sampling chambers (FIG. 5). Upon sampling, the membrane is removed and the collection material surface and the sorptive fillings are dried. If toxicity tests are to be carried out only, all surfaces (collection material and/or sorptive fillings) can be used for these tests. Where chemical analysis is to be carried out in addition the toxicity tests, a number of chambers which may optionally include the fillings should be reserved for this purpose, for example, a sampler could be divided in half, with one half being used for toxicity tests and the other half being reserved for chemical analysis.

The method for the toxicity tests follows the same method described for snap-shot sampling with a noteable difference. The difference relates to the surfaces to which the biological reporters are added. For snap-shot sampling, the reporters can be tested only on the surface of the chambers (the collection material), for time-integrated sampling, reporters can additionally be tested on the surface of the sorbent fillings or on both the surface of the chambers (the collection material) and the sorptive fillings. The decision for which one to use will depend on factors like the type of sorbent filling/coating (fillings and coating could select for different chemical classes), or whether a dose-response relationship is to be tested. If toxicity tests are to be done on the surface of the collection material, or on both the surface of the collection material and the sorptive fillings, biological reporters can be added directly to the sampling device. If the biological reporters are to be tested on the sorptive fillings only, these fillings will be placed into new chambers, such as the wells of tissue culture plates, prior to the addition to these chambers of the biological reporters.

Toxicity tests will indicate whether potentially harmful chemicals were accumulated by the sampling device during exposure to the sampling environment. This information would be analogous to the results, for example, of the rainbow trout lethality test or the Daphnia magna motility test if they were conducted upon exposure to a probe that contained the average concentration of the chemicals present during the entire sampling period. At present, such a representative probe cannot be obtained because, in order to determine average chemical concentrations over an extended period, numerous snap-shot samples would have to be analysed or the sampling be done on-line. The only currently available compromise is the extraction and elaborate clean-up of chemicals from the SPMD and the application of the extracts to the biological reporter cells (Sabaliunas et al., 1999).

Chemical analysis can be carried out on the sampling and exposure chambers in the manner described for chemical analysis after snap-shot sampling. Thus, chemical analysis can be done either by conventional analytical methods or through the use of a fluorescent plate reader. The concentrations determined can subsequently be used to calculate the average concentrations present during the entire sampling period (FIG. 4).

In addition to knowledge of the concentrations of compounds for which analysis is carried out, the combination of toxicological testing with chemical analysis can indicate the presence of toxic chemicals not yet analysed for and thus guide further testing and identification. The method for doing this is as described for snap-shot sampling.

The following non-limiting examples are illustrative of the present invention:

EXAMPLES

Example 1

Sorption of Fluoranthene to Polystyrene

In this example we provide an illustration of the sorption of fluoranthene to the polystyrene of tissue culture plates. For results please refer to FIG. 7.

For these experiments fluoranthene was dissolved in the aqueous medium, L-15/ex, to yield 297 nM (60 ng/ml) of fluoranthene. The fluoranthene solution was added once to empty wells of tissue culture plates, and 10 min, 2, 4, and 24 h later, the medium was removed and culture wells extracted with methanol in order to solubilize fluoranthene that had adsorbed to the culture surface. The concentration of fluoranthene in the methanol extracts was subsequently determined by high performance liquid chromatography (HPLC) and expressed as a percentage of the initial concentration, 297 nM. This plot shows that the polystyrene of tissue culture plates binds fluoranthene with high affinity (see also Schirmer et al., 1997). Similar results were found for other hydrophobic compounds (Hestermann et al., 2000; Longman and Buehring, 1986). If a single dose is applied (snap-shot sampling), equilibrium is reached within less than 24 h of exposure.

Example 2

Ability of Adsorbed BkF to Elicit EROD Induction

Figure 8:
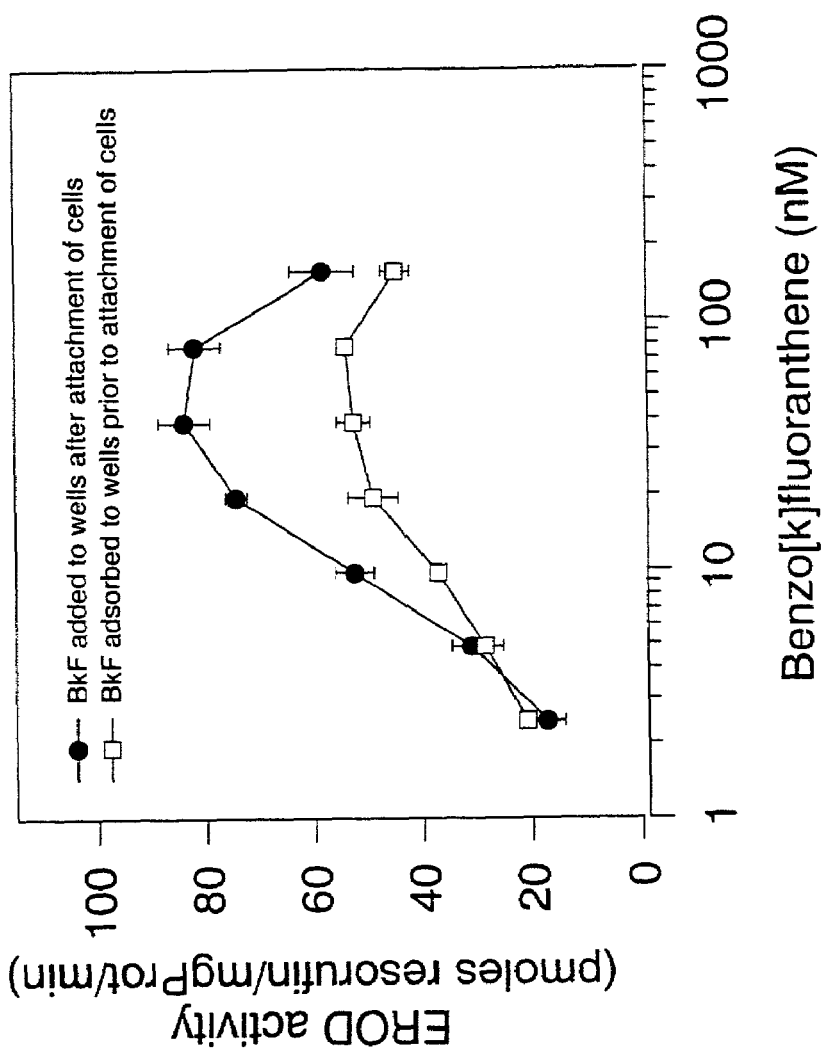
FIG. 8 illustrates the ability of sorbed benzo[k]fluoranthene to elicit EROD activity in a fish cell line; and, FIG. 9 illustrates the capacity of fractionation through sorption to reduce matrix effects and the ability of sorbed oil refinery effluent to elicit EROD activity in a fish cell line.

In this example we provide an illustration of the ability of adsorbed BkF to elicit of 7-ethoxyresorufin-o-deethylase (EROD) induction. Induction of EROD activity in a rainbow trout liver cell line (RTL-W1) by benzo[k]fluoranthene (BkF) that was either adsorbed to culture wells prior to cell attachment (method of the patent) or added to wells after cell attachment (conventional method). In order to adsorb BkF to the polystyrene surface of tissue culture plates (open symbol), 2.5 μl of BkF stock solutions were added to 500 μl per well of ddH$_2$O and left at room temperature for 24 h. The ddH$_2$O was removed, plates air dried and frozen at −80° C. until use. Upon thawing, cells were added and allowed to attach to the BkF-coating for 24 h prior to measurement of EROD activity. For adding BkF to cells that had already attached (closed symbol), 2.5 μl of BkF stock solutions were added directly to culture wells that contained the cells in 500 μl cell culture medium. Referring now to FIG. 8 it may be seen that, despite being sorbed to the surface of tissue culture wells, substances are capable of eliciting cellular responses that are otherwise obtained by adding the substances in dissolved form. Note that, although the magnitude of the responses were different for the two curves, EC50 values were similar with 10.4 nM and 8.6 nM for the sorbed and the dissolved BkF, respectively. In addition to this direct proof of the availability to reporter cells of sorbed chemicals, we have demonstrated the availability in indirect ways (Schirmer and Bols, 1999; Schirmer et al., 1998b). These previous indirect examples, from a different context than the present invention, demonstrated that sorption can be a problem in in vitro toxicological tests because tissue culture plates can adsorb the chemicals people want to study. It has not been shown any where, prior to the present disclosure that this "problem" could be turned into an advantage and into use of this principle for environmental sampling and subsequent toxicity testing, as described and claimed in the present specification.

Example 3

Reduced Matrix Effects and Ability of Adsorbed Oil Refinery Effluent to Elicit EROD Induction Induction of 7-ethoxyresorufin-o-deethylase (EROD) activity in a rainbow trout liver cell line (RTL-W1) by oil refinery effluent that was either adsorbed to culture wells prior to cell attachment (method of the patent) or added to wells after cell attachment (conventional method) is illustrated in this example. In order to initiate sorption, the effluent was added to the polystyrene surface of tissue culture plates onto which various volumes of ddH$_2$O had previously been added. With this method, various % of the effluent in the wells were obtained. The effluent was left on the plate at room temperature for 24 h. The ddH$_2$O was removed, and plates air dried. Subsequently, cells were added in 500 μl culture medium and allowed to attach to the effluent-coating for 24 h prior to measurement of EROD activity. For adding the effluent to cells that had already attached, effluent was added to the cells in culture plates and diluted with culture medium in order to obtain the various % of the effluent (Schirmer et al., 2000a). Referring now to FIG. 9, it may be seen that through the method of sorption, a fractionation technique is introduced that allows matrix effects of an environmental sample to be reduced. In addition, 100% effluent can be tested while with the conventional approach, the osmolality of most environmental samples allows the testing of only a limited concentration range. As was found for fish cells, a concentration of more than 50% of an environmental sample causes osmotic stress to the cells unless the osmolality of the sample is adjusted through the addition of salts (Schirmer et al., 2000a).

While the present invention has been described with reference to what are presently considered to be preferred examples, it is to be understood that the invention is not limited to the disclosed examples. To the contrary, the invention is intended to cover various modifications and equivalents included within the spirit and scope of the appended claims.

All publications, patents and patent applications referred to herein are incorporated by reference in their entirety to the same extent as if each individual publication, patent or patent application was specifically and individually indicated to be incorporated by reference in its entirety.

DETAILED REFERENCES

Arthur C L, Pawliszyn J. 1990. Solid Phase Microextraction with thermal desorption using fused silica optical fibers. Analytical Chemistry 62, 2145–2148.

Baun A, Jensen S D, Bjerg P L, Christensen T H, Nyholm N. 2000. Toxicity of organic chemical pollution in groundwater downgradient of a landfill (Grinsted, Denmark). Environmental Science and Technology 34, 1647–1652.

Bitton G, Koopman B. 1992. Bacterial and enzymatic bioassays for toxicity testing in the environment. Reviews in Environmental Contamination and Toxicology 125, 1–22.

Bols N C, Schirmer K, Joyce E M, Dixon D G, Greenberg B M, Whyte J J. 1999. Ability of polycyclic aromatic hydrocarbons to induce 7-ethoxyresorufin-O-deethylase activity in a trout liver cell line. Ecotoxicology and Environmental Safety 44, 118–128.

Bosveld A T, Kennedy S W, Seinen W, van den Berg M. 1997. Ethoxyresorufin-O-deethylase (EROD) inducing potencies of planar chlorinated aromatic hydrocarbons in primary cultures of hepatocytes from different developmental stages of the chicken. Archives of Toxicology 71, 746–750.

Cronin M T, Schultz T W. 1997. Validation of *Vibrio fisheri* acute toxicity data: mechanism of action-based QSARs for non-polar narcotics and polar narcotic phenols.

Fairchild J F, Ruessler D S, Haverland P S, Carlson A R. 1997. Comparative sensitivity of *Selenastrum capricornutum* and Lemna minor to sixteen herbicides. Archives of Environmental Contamination and Toxicology 32, 353–357.

Grant G M, Shaffer K M, Kao W Y, Stenger D A, Pancrazio J J. 2000. Investigation of in vitro toxicity of jet fuels JP-8 and Jet A Drug Chemistry and Toxicology 23, 279–291.

Haubenstricker M E, Meier P G, Mancy K H, Brabec M J. 1990. Rapid toxicity testing based on yeast respiratory activity. Bulletin of Environmental Contamination and Toxicology 44, 669–674.

Hestermann E V, Stegeman J J, Hahn M E. 2000. Serum alters the uptake and relative-potencies of halogenated aromatic hydrocarbons in cell culture bioassays. Toxicological Sciences 53, 316–325.

Huckins J N, Manuweera G K, Petty J D, Mackay D, Lebo J A. 1993. Lipid-containing semipermeable membrane devices for monitoring organic contaminants in water. Environmental Science and Technology 27, 2489–2496.

Longman S M, Buehring G C. 1986. A method for measuring steroid sorption to tissue culture plasticware. Journal of Tissue Culture Methods 10, 253–255.

Lynn D H, Gilron G L. 1992. A brief review of approaches using ciliated protists to assess aquatic ecosystem health. Journal of Aquatic Ecosystem Health 1, 263–270.

Martin H, Piepenbrink M, Grathwohl P. 1999. Ceramic dosimeter for contaminant monitoring. In Johnston, C. D. (ed.): Contaminated site remediation: Challenges posed by urban and industrial contaminants. (Int. Conference, Fremantle, Western Australia, March 1999), 196–198.

Sabaliunas D, Ellington J, Sabaliuniene I. 1999. Screening bioavailable hydrophobic toxicants in surface waters with semipermeable membrane devices: role of inherent oleic acid in toxicity evaluations. Ecotoxicology and Environmental Safety 44, 160–167.

Safe S. (1990) Polychlorinated biphenyls (PBCs), dibenzo-p-dioxins (PCDDs), dibenzofurans (PCDFs), and related compounds: Environmental and mechanistic considerations which support the development of toxic equivalency factors (TEFs). Critical Reviews in Toxicology 21, 51–88.

Schirmer K, Chan A G J, Greenberg B M, Dixon D G, Bols N C. 1998. Ability of 16 priority PAHs to be photocytotoxic to a cell line from the rainbow trout gill. Toxicology 127, 143–155.

Schirmer K, Chan A G J, Bols N C. 1998. Role of sorption in the in vitro toxicity of fluoranthene. 19th Annual Meeting of the Society of Environmental Toxicology and Chemistry, Charlotte, N.C., USA, November 15–19.

Schirmer K, Chan A G J, Greenberg B M, Dixon D G, Bols N C. 1997. Methodology for demonstrating and measuring the photocytotoxicity of fluoranthene to fish cells in culture. Toxicology in Vitro 11, 107–119.

Scroggins R, Rodrigue D. 2000. Standardization and Harmonization of biological test methods in Canada. 10$^{th}$ Symposium on Environmental Toxicity and Risk Assessment: Science, Policy, and Standardization—Implications for Environmental Decisions, April 10-12, Toronto, Ontario, Canada, p.39.

Wang W. 1990. Literature review on duckweed toxicity testing. Environmental Research 52, 7–22.

Whitlock J P. 1999. Induction of cytochrome P4501A1. Annual Reviews in Pharmacology and Toxicology 39, 103–125.

TABLE 1

Comparison snap-shot vs. time-integral sampling

| | Snap-shot | Time-integrated |
|---|---|---|
| When to use? | When total concentration of chemical(s) are to be determined at respective point in time | When average concentration of chemical(s) are to be determined for long exposure times |
| Where to use? | For probing chemicals dissolved in aqueous and gaseous media | For probing chemicals dissolved in aqueous or gaseous media |
| What is the advantage over taking a sample the conventional way (e.g. getting a bucket of water?) | A certain group of chemicals can be selected for (depending on sampler coating); this can be done either directly in the field or upon exposure of the sampler to the probe in the lab | A certain group of chemicals can be selected for (depending on sampler coating or filling) Average concentration of chemical(s) present during entire sampling period can be determined Chemicals are being concentrated, which makes for easier detection in chemical analysis or toxicological tests |
| Do similar sampling strategies exist? | Solid phase microextraction (SPME) potentially Semipermeable membrane device (SPMD) (if equilibrium can be reached quickly) | Dosimeter (see Grathwohl patent) Semipermeable membrane device (SPMD) (if non-equilibrium uptake can be maintained) (see Huckins et al. patents) |

Schirmer K, Tom D J, Bols N C, Sherry J P. 2000a. Ability of fractionated petroleum refinery effluent to elicit cyto- and photocytotoxic responses and to induce 7-ethoxyresorufin-O-deethylase activity in fish cell lines. The Science of the Total Environment 271, 61–78.

Schirmer K, Chan A G J, Bols N C. 2000b. Transitory metabolic disruption and cytotoxicity elicited by benzo[a]pyrene in two cell lines from rainbow trout liver. Journal of Biochemical and Molecular Toxicology 14, 262–276.

Schirmer K, Herbrick J S, Greenberg M B, Dixon D G, Bols N C. 1999. Use of fish gill cells in culture to evaluate the cytotoxicity and photocytotoxicity of intact and photo-modified creosote. Environmental Toxicology and Chemistry 18, 1277–1288.

Schirmer K, Bols N C. 1999. Sorption, distribution and bioavailability of fluoranthene in microwell plates. 9th Annual Meeting of the Society of Environmental Toxicology and Chemistry, Leipzig, Germany, May 25–29, 2e/P005.

We claim:

1. A method for sampling and monitoring toxicity in an environmental sample comprising the steps of:

(a) providing a device comprising a chamber with an entry port covered by a membrane, the device having a collection material in the chamber for adsorbing at least one chemical from the environmental sample, and contacting said device with the environmental sample;

(b) removing the device from the environmental sample and adding a reporter comprising a cell or an organism capable of living in the chamber and/or the collection material to the chamber;

(c) incubating the reporter;

(d) assaying the reporter to measure an outcome showing whether the cell or organism is detrimentally affected by a toxicological response to the chemical to determine whether the chemical was adsorbed in the chamber.

2. The method of claim 1 further comprising extracting the chemical from the collection material and performing a chemical analysis of the chemical to provide its concentration and identity.

3. The method according to claim 1 further comprising providing a filler sorbent to increase the sorptive capacity of the chamber.

4. The method according to claim 1 wherein the device comprises a plurality of chambers and at least some of the chambers contain varying amounts of a filler sorbent and at least some of the chambers having the filler sorbent are treated to obtain a dose-response profile.

5. The method according to claim 1 wherein the device comprises a plurality of chambers and the method further comprises providing a filler sorbent in some of the chambers.

6. The method of claim 1 wherein the membrane comprises a semi-permeable membrane.

7. The method of claim 6, wherein the chemical travels essentially unidirectionally into the chamber and a concentration gradient for the chemical exists across the semi-permeable membrane.

8. The method according to claim 1 further comprising the step of desorbing the chemical from the substrate.

9. The method according to claim 8 wherein desorbing the chemical comprises thermal desorption and/or contacting the chemical with a solvent.

10. The method according to claim 8 further comprising conducting a chemical analysis to identify and/or quantitate the chemical.

11. The method according to claim 10 wherein the chemical analysis comprises time-integrated and/or snap-shot sampling.

12. The method of claim 1 wherein the cell or organism desorbs the chemical.

13. The method of claim 1 wherein the cell is selected from the group consisting of an animal cell, a mammalian cell, a bird cell, a fish cell, a plant cell, an algal cell, a daphnid cell, a yeast cell, a bacterial cell, a duckweed cell, a selenastrum cell and a Vibria fisheri cell.

14. The method of claim 1 wherein the cell is located in a cell culture, or a multicellular organism.

15. The method of claim 1 wherein the outcome is selected from the group consisting of:
 (i) loss of vitality;
 (ii) loss of functionality;
 (iii) disruption and/or loss of cell metabolic activity;
 (iv) induction or disruption of an enzyme; and
 (v) expression of a gene.

16. The method of claim 15 wherein the loss of functionality comprises loss of motility.

17. The method of claim 15 wherein the disruption of cell metabolic activity comprises modulation of cell growth.

18. The method of claim 15 wherein the induction of the enzyme comprises induction of 7-ethoxyresorufin-O-deethylase (EROD) activity.

19. A method of determining the concentration of a substance in an environmental sample comprising the steps of:
 (a) placing a device comprising a chamber with an entry port covered by a membrane, the device having a collection material in the chamber for adsorbing at least one chemical from the environmental sample, and contacting the device with the environmental sample;
 (b) removing the device from the environmental sample and adding a reporter comprising a cell or an organism capable of living in the chamber and/or the collection material to the chamber of the device;
 (c) incubating the reporter;
 (d) assaying the reporter to measure an outcome showing whether the cell or organism is detrimentally affected by a toxicological response to the chemical and determining a quantity of the chemical adsorbed in the chamber; and,
 (e) calculating the concentration of the chemical in the environmental sample based on the determination.

20. The method of claim 19 further comprising extracting the chemical from the collection material and performing a chemical analysis of the chemical to provide its concentration and identity.

21. The method according to claim 19 further comprising providing a filler sorbent to increase the sorptive capacity of the chamber.

22. The method according to claim 19 wherein the device comprises a plurality of chambers and at least some of the chambers contain varying amounts of a filler sorbent and at least some of the chambers having the filler sorbent are treated to obtain a dose-response profile.

23. The method according to claim 19 wherein the device comprises a plurality of chambers and the method further comprises providing a filler sorbent in some of the chambers.

24. The method of claim 19 wherein the membrane comprises a semi-permeable membrane.

25. The method of claim 24, wherein the chemical travels essentially unidirectionally into the chamber and a concentration gradient for the chemical exists across the semi-permeable membrane.

26. The method according to claim 19 further comprising the step of desorbing the chemical from the substrate.

27. The method according to claim 26 wherein desorbing the chemical comprises thermal desorption and/or contacting the chemical with a solvent.

28. The method according to claim 26 further comprising conducting a chemical analysis to identify and/or quantitate the chemical.

29. The method according to claim 28 wherein the chemical analysis comprises time-integrated and/or snap-shot sampling.

30. The method of claim 19 wherein the cell or organism desorbs the chemical.

31. The method of claim 19 wherein the cell is selected from the group consisting of an animal cell, a mammalian cell, a bird cell, a fish cell, a plant cell, an algal cell, a daphnid cell, a yeast cell, a bacterial cell, a duckweed cell, a selenastrum cell and a Vibrio fisheri cell.

32. The method of claim 19 wherein the cell is a single cell located in a cell culture, or a multicellular organism.

33. The method of claim 19 wherein the outcome is selected from the group consisting of:
 (i) loss of vitality;
 (ii) loss of functionality;
 (iii) disruption and/or loss of cell metabolic activity;
 (iv) induction or disruption of an enzyme; and
 (v) expression of a gene.

34. The method of claim 33 wherein the loss of functionality comprises loss of motility.

35. The method of claim 33 wherein the disruption of cell metabolic activity comprises modulation of cell growth.

36. The method of claim 33 wherein the induction of the enzyme comprises induction of 7-ethoxyresorufin-O-deethylase (EROD) activity.

* * * * *